US010563162B2

(12) United States Patent
Flory et al.

(10) Patent No.: US 10,563,162 B2
(45) Date of Patent: *Feb. 18, 2020

(54) MICROBIAL ELECTRO-PHOTOSYNTHESIS

(71) Applicant: Arizona Board of Regents on behalf of Arizona State University, Scottsdale, AZ (US)

(72) Inventors: Justin Flory, Scottsdale, AZ (US); Petra Fromme, Mesa, AZ (US); Willem Vermaas, Tempe, AZ (US); Bruce Rittman, Tempe, AZ (US); Cesar Torres, Tempe, AZ (US); Thomas Moore, Scottsdale, AZ (US); Ana Moore, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/539,961

(22) Filed: Aug. 13, 2019

(65) Prior Publication Data

US 2019/0376018 A1  Dec. 12, 2019

Related U.S. Application Data

(63) Continuation of application No. 14/972,977, filed on Dec. 17, 2015, now Pat. No. 10,385,304.

(60) Provisional application No. 62/093,863, filed on Dec. 18, 2014.

(51) Int. Cl.
*C12M 1/42* (2006.01)
*C12N 1/12* (2006.01)
*C12N 13/00* (2006.01)
*C12M 1/00* (2006.01)

(52) U.S. Cl.
CPC .............. *C12M 35/02* (2013.01); *C12M 1/42* (2013.01); *C12M 21/02* (2013.01); *C12M 43/00* (2013.01); *C12N 1/12* (2013.01); *C12N 13/00* (2013.01)

(58) Field of Classification Search
None
See application file for complete search history.

(56) References Cited

U.S. PATENT DOCUMENTS

| 8,753,840 | B2 | 6/2014 | Vermaas | |
| 2003/0138674 | A1* | 7/2003 | Zeikus | C12N 13/00 429/2 |
| 2011/0053216 | A1 | 3/2011 | Vermaas | |
| 2013/0130341 | A1* | 5/2013 | Liao | C12N 9/0006 435/156 |
| 2014/0377857 | A1* | 12/2014 | Liao | C12M 21/12 435/297.1 |

OTHER PUBLICATIONS

Wang, Q. J.; Singh, A.; Li, H.; Nedbal, L; Whitmarsh, J., et al., Net light-induced oxygen evolution in photosystem I deletion mutants of the *Cyanobacterium synechocyctis* sp. PCC 6803. Biochim. Biophys. Acta 2012, 1817, 792-801.
Wender, B. A., R. W. Foley, T. A. Hottle, J. T. P. Seager , et al., Anticipatory life-cycle assessment for responsible research and innovation. J Responsible Innovation. 2014, vol. 1, 200-207.
Wender, B. A., Foley, R.W., Seager, T.P., and Wiek, A. Anticipatory governance and anticipatory life cycle assessment of single wall carbon nanotube anode lithium ion batteries. J Nanotechnology Law Bus. 2013. 9(3), 201-216.
Gutowski, T. G.; Branham, M. S.; Sekulic, D. P., et al. Thermodynamic analysis of resources used in manufacturing processes. Environ. Sci. Technol. 2009, 43, 1584-1590.
Nemet, G. F. Beyond the learning curve: factors influencing cost reductions in photovoltaics. Energy Policy. 2006, 34, 3218-3232.
Soratana, K.; Landis, A. E. Evaluating industrial symbiosis and algae cultivation from a life cycle perspective. Bioresour. Technol. 2011, 102, 6892-6901.
Soratana, K.; Barr, W. J.; Landis, A. E. Effects of co-products on the life-cycle impacts of microalgal biodiesel. Bioresour. Technol. 2014, 159, 157-166.
Fthenakis, V.; Frischknecht, R., Raugei, M.; Kim, H. C.; de Wild-Scholten, M., et al. Methodology guidelines on life-cycle assessment of photovoltaic electricity. Int. Energy Agency 2011.
Fthenakis, V.; Kim, H. C.; Stucki, M., et al., Int. Energy Agency PVPS Task 12, Rep. T12, Life cycle inventories and life cycle assessments of photovoltaic systems. 2011.
de Wild-Scholten, M. J. Energy payback time and carbon footprint of commercial photovoltaic systems. Sol. Energy Mater. Sol. Cells 2013, 119, 296-305.
Laurens, L. M. L.; Dempster, T. A; Jones, H. D. T.; Gloe, L. M., et al. Algal biomass constituent analysis: Method uncertainties and investigation of the underlying measuring chemistries. Anal. Chem. 2012, 84, 1879-1887.
Rogers, K.; Seager, T. P. Environmental decision-making using life cycle impact assessment and stochastic multiattribute decision analysis: A case study on alternative transportation fuels. Environ. Sci. Technol. 2009, 43, 1718-1723.
Prado-Lopez, V.; Seager, T. P.; Chester, M.; Tylock, S., et al., Stochastic multi-attribute analysis (SMAA) as an interpretation method for comparative life-cycle assessment (LCA). Int. J. Life Cycle Assess. 2013, 19, 405-416.
Liu B.; Liu, S.; Arunakumara, K. K. I. U.; Zhang, X. J. Optimum conditions for transformation of *synechocystis* sp. PCC 6803. Microbiol. 2007, 45, 241-245.

(Continued)

*Primary Examiner* — Robert J Yamasaki
*Assistant Examiner* — Charles Zoltan Constantine
(74) *Attorney, Agent, or Firm* — Quarles & Brady LLP; Jessica L. Lewis

(57) ABSTRACT

Methods and apparatus for growing photosynthetic organisms lacking Photosystem II (PSII) function using externally supplied electrons shuttled into the organism using redox mediators to improve photosynthetic output and to produce and recover chemicals of interest. By removing PSII, all PAR photons are funneled toward Photosystem I, thereby significantly increasing the theoretical photon utilization efficiency for $CO_2$ fixation, energy storage and the capacity to synthesize valuable chemicals. Additional genetic modification can be performed to insert or enhance specific metabolic pathways to generate products of commercial interest.

13 Claims, 3 Drawing Sheets

(56) References Cited

OTHER PUBLICATIONS

Grobbelaar, J. U. Photosynthetic characteristics of Spirulina platensis grown in commercial-scale open outdoor raceway ponds: what do the organisms tell us? J. Appl. Phycol. 2007, 19, 591-598.

Peterhansel, C. et al. Photorespiration. 2010. The Arabidopsis Book. 1-24.

Cao, X. et al. A completely anoxic microbial fuel cell using a photo-biocathode for cathodic carbon dioxide reduction. 2009. Energy Environ. Sci. 2, 498-501.

Powell, E. E., Mapiour, M. L., Evitts, R. W. & Hill, G. a. Growth kinetics of Chlorella vulgaris and its use as a cathodic half cell. 2009. Bioresour. Technol. 100, 269-274.

Frigaard, N. U., "Gene Inactivation in the *Cyanobacterium synechococcus* sp. PCC 7002 and the Green Sulfur Bacterium Chlorobium tepidum Using in Vitro-Made DNA Constructs and Natural Transformation", Methods in Molecular Biology, vol. 274, pp. 325-340 (2004).

Kindle, K. L., "High-frequency nuclear transformation of Chlamydomonas reinhardtii", Proceedings National Academy of Science, vol. 87, pp. 1228-1232 (Feb. 1990).

Lu, Y., "Identification and Roles of Photosystem II Assembly, Stability,and Repair Factors in *Arabidopsis*", Frontiers in Plant Science, vol. 7, Article 168, pp. 1-27 (Feb. 2016).

Bogorad, L. Phycobiliproteins and complementary chromatic adaptation. Annu. Rev. Plant Physiol. 1975, 26, 369-401.

Wang, B.; Pugh, S.; Nielsen, D. R.; Zhang, W.; Meldrum, D. R. Engineering cyanobacteria for photosynthetic production of 3-hydroxybutyrate directly from $CO_2$. Metab. Eng. 2013, 16, 68-77.

Air Transport Action Group. Reducing Emissions From Aviation Through Carbon—Neutral Growth From 2020; 2013.

Nevin, K. P.; Woodard, T. L.; Franks, A. E, Summers, S. M. & Lovley, D. R. Microbial electrosynthesis : feeding microbes electricity to convert carbon dioxide and water to multicarbon extracellular organic compounds. MBio 1(2), e00103-10 (2010).

Vermaas, W. F. J.; Williams, J. G. K.; Arntzen, C. J. Sequencing and modification of psbB, the gene encoding the CP-47 protein of Photosystem II, in the cyanobacterium Synechocystis 6803. Plant Mol. Biol. 1987, 8, 317-326.

Chavez-Santoscoy, A.; Vermaas, W. F. J., et al. Application of aqueous two-phase systems for the potential extractive fermentation of cyanobacterial products. Chem. Eng. Technol. 2010, 33, 177-182.

Artero, V., Fontecave, M. Solar fuels generation and molecular systems: is it homogeneous or heterogeneous catalysis? Chem. Soc. Rev. 2013, 42, 2338-2356.

Kanan, M. W.; Nocera, D. G. In situ formation of an oxygen-evolving catalyst in neutral water containing phosphate and $Co2+$. Science 2008, 321, 1072-1075.

Jiao, F.; Frei, H. Nanostructured cobalt oxide clusters in mesoporous silica as efficient oxygen-evolving catalysts. Angew. Chemie Int. Ed. 2009, 121, 1873-1876.

Wee, T.-L.; Moore, A. L.; Moore, T. A; Scaiano, J. C., et al., Photochemical synthesis of a water oxidation catalyst based on cobalt nanostructures. J. Am. Chem. Soc. 2011, 133, 16742-16745.

Blankenship, R. E. et al. Comparing photosynthetic and photovoltaic efficiencies and recognizing the potential for Improvement. Science 2011, 332, 805-809.

Sacksteder, C. A; Kanazawa, A; Kramer, D. M., et al. The proton to electron stoichiometry of steady-state photosynthesis in living plants: A proton-pumping Q cycle is continuously engaged. Proc. Natl. Acad. Sci. U. S. A. 2000, 97, 14283-14288.

Kramer, D. M.; Cruz, J. a; Kanazawa, A. Balancing the central roles of the thylakoid proton gradient. Trends Plant Sci. 2003, 8, 27-32.

Raven, J. A; Beardall, J.; Giordano, M. Energy costs of carbon dioxide concentrating mechanisms in aquatic organisms. Photosynth. Res. 2014, 121, 111-124.

Niyogi, K. K.; Grossman, A. R.; Björkman, O. *Arabidopsis* mutants define a central role for the Xanthophyll cycle in the regulation of photosynthetic energy conversion. Plant Cell 1998, 10, 1121-1134.

Niyogi, K. K.; Truong, T. B. Evolution of flexible non-photochemical quenching mechanisms that regulate light harvesting in oxygenic photosynthesis. Curr. Opin. Plant Biol. 2013, 16, 307-314.

Kirilovsky, D.; Kerfeld, C. A. The orange carotenoid protein in photoprotection of photosystem II in cyanobacteria. Biochim. Biophys. Acta 2012, 1817, 158-166.

Rakhimberdieva, M. G.; Elanskaya, I. V; Vermaas, W. F. J.; Karapetyan, N. V. Carotenoid-triggered energy dissipation in phycobilisomes of *synechocystis* sp. PCC 6803 diverts excitation away from reaction centers of both photosystems. Biochim. Biophys. Acta 2010, 1797, 241-249.

Raven, J. a. Physiol. The cost of photoinhibition. Plant. 2011, 142, 87-104.

Wigmosta, M. S.; Coleman, A. M.; Skaggs, R. J.; Lane, L. J. et al., National microalgae biofuel production potential and resource demand. Water Resour. Res. 2011, 47, W00H04.

Dinamarca, J.; Shlyk-Kemer, O.; Kaftan, D.; Goldberg, E.; Scherz, A., et al. Double mutation in Photosystem II reaction centers and elevated $CO_2$ grant thermotolerance to mesophilic Cyanobacterium. PLoS One 2011, 6, e28389.

Davis, R.; Aden, A.; Pienkos, P. T. Techno-economic analysis of autotrophic microalgae for fuel production. Appl. Energy 2011, 88, 3524-3531.

Lawrence, R. M. Recombinant Expression, Purification, and Reconstitution of the Chloroplast ATP Synthase c-subunit Ring, 2011, Dissertation.

Moses, C. A. Comparative Evaluation of Semi-synthetic Jet Fuels; 2008.

Torres, C. I.; Krajmalnik-Brown, R.; Rittmann, B. E., et al., Selecting anode-respiring bacteria based on anode potential: phylogenetic, electrochemical, and microscopic characterization. Environ. Sci. Technol. 2009, 43, 9519-9524.

Parameswaran, P.; Torres, C. I.; Rittmann, B. E., et al., Syntrophic interactions among anode respiring bacteria (ARB) and non-ARB in a biofilm anode: electron balances. Biotechnol. Bioeng. 2009, 103, 513-523.

Badalamenti, J. P.; Torres, C. I.; Krajmalnik-Brown, R. Light-responsive current generation by phototrophically enriched anode biofilms dominated by green sulfur bacteria. Biotechnol. Bioeng. 2013, 110, 1020-1027.

Vermaas, W. F. J.; Rutherford, A. W.; Hansson, O. Site-directed mutagenesis in photosystem II of the *Canobacterium synechocystis* sp. PCC 6803: Donor D is a tyrosine residue in the D2 protein. Proc. Natl. Acad. Sci. U. S. A. 1988, 85, 8477-8481.

Jordan, P.; Fromme, P.; Witt, H. T.; Klukas, O.; Saenger, W.; Krauss, N. Three-dimensional structure of cyanobacterial photosystem I at 2.5 A resolution. Nature 2001, 411, 909-917.

Bensasson, R.; Land, E; Moore, A. Mimicry of antenna and photoprotective carotenoid functions by a synthetic carotenoporphyrin. Nature 1981, 290, 329-332.

Torres, C. I.; Kato Marcus, A.; Rittmann, B. E. Proton transport inside the biofilm limits electrical current generation by anode-respiring bacteria. Biotechnol. Bioeng. 2008, 100, 872-881.

Rich, P.; Madgwick, S.; Moss, D. Biochim. The interactions of duroquinol, DBMIB and NQNO with chloroplast cytochrome bf complex. Biophys. Acta 1991, 1058, 312-328.

Wood, P.; Bendall, D. The reduction of plastocyanin by plastoquinol-1 in the presence of chloroplasts. Eur. J. Biochem. 1976, 344, 337-344.

Sekar, N.; Umasankar, Y.; Ramasamy, R. P. Photocurrent generation by immobilized cyanobacteria via direct electron transport in photo-bioelectrochemical cells. Phys. Chem. Chem. Phys. 2014, 16, 7862-7871.

Sener, M. K.; Lu, D.; Ritz, T.; Park, S.; Fromme, P.; Schulten, K. J. Robustness and optimality of light harvesting in Cyanobacterial photosystem I. Phys. Chem. B 2002, 106, 7948-7960.

Verschoor, A. M.; Van Dijk, M. a.; Huisman, J.; Van Donk, E. Elevated $CO_2$ concentrations affect the elemental stoichiometry and species composition of an experimental phytoplankton community. Freshw. Biol. 2013, 58, 597-611.

Liu, T.; Wang, J.; Hu, Q.; Cheng, P.; Ji, B.; Liu, J.; Wang, H., et al., Attached cultivation technology of microalgae for efficient biomass feedstock production. Bioresour. Technol. 2013, 127, 216-222.

(56) References Cited

OTHER PUBLICATIONS

Zhu X.-G.; Long, S. P.; Ort, D. R. Improving photosynthetic efficiency for greater yield. Annu. Rev. Plant Biol. 2010, 61,235-261.

Weyer, K. M.; Bush, D. R.; Darzins, A.; Willson, B. D. Theoritical maximum algal oil production. BioEnergy Res. 2010, 3, 204-213.

Ng, V. W.; Sanders, S. R. A high-efficiency wide-input-voltage range switched capacitor point-of-load DC-DC converter. IEEE Trans. Power Electron. 2013, 28, 4335-4341.

Bolinger, M.; Weaver, S. Utility-Scale Solar 2012; An empirical analysis of project cost, performance, and pricing trends in the United States. 2013; pp. 1-36.

Wesoff, E Anatomy of a Deal: 4-Cent-per-Kilowatt-Hour Solar in Palo Alto http://www.greentechmedia.com/ articles/read/Anatomy-of-a-PPA-4-Cent-Per-Kilowatt-Hour-Solar-in-Palo-Alto-CA. [Accessed May 2014].

U.S. Department of Energy. $1/W Photovoltaic Systems; 2010.

Villano, M., et al., Bioelectrochemical reduction of CO2 to CH4 via direct and indirect extracellular electron transfer by a hydrogenophilic methanogenic culture. Bioresour. Technol. 2010, 101, 3085-3090.

Hanna, M. C.; Nozik, A. J. Solar conversion efficiency of photovoltaic and photoelectrolysis cells with carrier multiplication absorbers. J. Appl. Phys. 2006, 100, 074510.

Marcus, Y.; Altman-Gueta, H.; Wolff, Y.; Gurevitz, M. Rubisco mutagenesis provides new insight into limitations on photosynthesis and growth in Synechocystis PCC6803. J. Exp. Bot. 2011, 62, 4173-4182.

Kauny, J.; Sétif, P. NADPH fluorescence in the *Cyanobacterium synechocystis* sp. PCC 6803: A versatile probe for in vivo measurements of rates, yields and pools. Biochim. Biophys. Acta 2014, 1837, 792-801.

Lüneberg, J.; Fromme, P.; Jekow, P.; Schlodder, E. Spectroscopic characterization of PS I core complexes from thermophilic *synechococcus* sp. FEBS Lett. 1994, 338, 197-202.

Chauhan, D.; Folea, I. M.; Jolley, C. C.; Kouril, R.; Fromme, P., et al., A novel photosynthetic strategy for adaptation to low-iron aquatic environments. Biochemistry 2011, 50, 686-692.

White, A. M.; Daly, D. S.; Zangar, R. C. Analysis of high-throughput ELISA microarray data. Methods Mol. Biol. 2011, 694,191-211.

* cited by examiner

MICROBIAL ELECTRO-PHOTOSYNTHESIS

CROSS-REFERENCE TO RELATED APPLICATIONS

This application is a continuation of U.S. patent application Ser. No. 14/972,977, filed on Dec. 17, 2015, which claims priority to U.S. Provisional Patent Application No. 62/093,863, filed Dec. 18, 2014, the entire contents of which are incorporated herein in their entirety by reference.

STATEMENT OF GOVERNMENT RIGHTS

This invention was made with government support under DE-SC0001016 awarded by the Department of Energy. The government has certain rights in the invention.

BACKGROUND OF THE INVENTION

Over 2 billion year ago, the evolution of oxygenic photosynthesis completely transformed the earth's ecosystems by enabling the extraction of electrons and protons from abundant sources of water using sunlight and releasing $O_2$ into the previously anaerobic atmosphere. Solar-driven water oxidation is uniquely performed in nature by the Photosystem II (PSII) complex; however, under normal operation PSII generates and is damaged by reactive oxygen species, which also damage other cell components. Moreover, the oxygen released during photosynthesis induces stress to the organism and impairs other important metabolic functions, such as $CO_2$ fixation and $H_2$ production. The net output of the light reactions of photosynthesis is to produce ATP and NADPH, which are used by the organism to make a wide array of complex organic molecules, many of which are cost prohibitive to make synthetically for commercial applications.

SUMMARY OF THE INVENTION

While photosynthetic microorganisms offer a promising route to generate sustainable transportation fuels and petroleum substitutes using solar energy, boosting their photosynthetic efficiency will help ensure its economic viability. A major source of inefficiency is that photosynthetically active radiation (PAR, 400-700 nm) constitutes less than half of the solar energy reaching the earth's surface. Photosynthetic organisms use PAR to oxidize water as a source of electrons in photosynthesis. Photovoltaics (PV) capture twice as many photons as photosynthetic pigments do and can be used along with synthetic catalysts to extract electrons from water. However, artificial systems have yet to realize the capacity of photosynthesis to produce complex molecules and drop-in transportation fuels.

Integration of phototrophic and heterotrophic microorganisms into electrochemical cells has enabled selection of organisms that donate electrons to or receive electrons from an electrode, directly or through a mediator, to produce electricity or to promote various metabolic activities (e.g., biosynthesis, bioremediation). Microbial electrosynthesis cells (MEC) use microorganisms to synthesize simple organic molecules from electrons injected directly from a cathode poised at significant reducing potentials. However, the required negative potentials lower the thermodynamic efficiency and may produce undesired products, such as $H_2$.

Microbial electro-photosynthesis (MEPS) leverages the efficiency of artificial systems to use sunlight to extract electrons from water and the capacity of photosynthetic organisms to capture and convert $CO_2$ into valuable products and fuels. The electrons are shuttled using redox mediators from a cathode of an electrochemical cell into a photobioreactor (PBR) containing a phototroph lacking or having minimal PSII function to promote accepting external electrons. Expanding MECs to include photosynthetic organisms leverages the capability of natural photosynthesis to use sunlight to boost an electron's reducing potential (more negative) in a controlled manner, where it can be shuttled into the desired metabolic pathways.

In the MEPS system, a cyanobacterial strain, such as a *Synechocystis* sp. PCC 6803 mutant lacking PSII, is provided with electrons from an artificial water-oxidation catalyst, which are shuttled into the organism using chemical redox mediators. By removing PSII, all PAR photons are funneled toward PSI, thereby significantly increasing the theoretical photon utilization efficiency for $CO_2$ fixation. The catalyst can be driven directly by light using a photovoltaic (PV) device or from virtually any source of electricity in order to leverage ongoing developments in energy technologies. Low-cost electricity-storage technologies are required to expand solar installations so that they make up a significant fraction of total energy production due to imbalance of supply and demand. Chemical mediators are selected and designed to reduce naturally occurring electron carriers, such as plastoquinone, within photosynthetic membranes; these electrons are then be used by the photosynthetic electron transport chain (PETC) in lieu of electrons generated by PSII.

The *Synechocystis* mutant retains PSI, which uses light energy to boost the reducing power of these electrons to enable carbon fixation, yielding 1) biomass, 2) complex, high-energy transportation fuel feedstock, which are not efficiently generated by microorganisms from electricity alone, 3) ATP production, and 4) other reduction reactions, such as nitrate reduction.

MEPS has the ability to significantly increase the productivity of photosynthetic organisms to make products and fuels, reduce water and nutrient usage, as well as to capture and recycle $CO_2$. Thus, MEPS helps address the critical domestic and global challenges of energy security and climate change.

The photobioreactor used with embodiments described herein may be selected from a vertical tubular, air-lift, horizontal tubular, flat-panel, or plastic-bag. Moreover, the anode may include a catalyst to promote water oxidation, such as platinum, platinum-carbon, cobalt phosphate, $C_{O3}O_4$ nanoparticles, and $C_{O2}O_3$ nanoparticles. The cathode may be made of carbon felt or carbon fiber. And the phototrophic organism may be a mutant cyanobacterium *Synechocystis* sp. PCC 6803 with no or minimal PSII function, a mutant of any species of cyanobacterium or alga lacking or with minimal PSII function (i.e., 10% or less of wild type activity), or any species of green sulfur bacterium, green non-sulfur bacterium, purple sulfur bacterium, purple non-sulfur bacterium or heliobacterium.

DETAILED DESCRIPTION OF THE INVENTION

In some embodiments, a strain of cyanobacteria, algae, or any other photosynthetic microorganism that retains Photosystem I, but lacks the Photosystem II function, is used to synthesize fuels and/or products with electrons provided from an external water oxidation catalyst rather than photosynthetic water splitting.

In other embodiments, directed evolution of a photosynthetic organism that retains Photosystem I, but lacks the Photosystem II function, is used to further boost productivity of photosynthetically generated fuels and chemicals using electricity. In still other embodiments, light and electricity assisted growth and synthesis of fuels and products are utilized.

Figure 3:
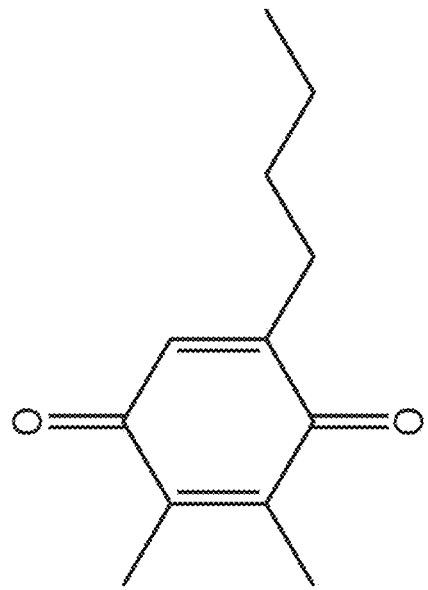
FIG. 3 shows a plastoquinone variant with a four-carbon alkyl tail (C4).

In further embodiments, customized quinone-type mediators for injecting electrons into the photosynthetic electron transport chain are utilized, for example, plastoquinone variants are used for shuttling electrons into organisms, as shown in FIG. 3, where is the native isoprenoid tail of PQ is replaced with a synthetically simpler alkyl tail of various lengths (e.g., 2 to 9 carbons) to adjust the requirements for solubility and interfacing with native electron carriers.

According to an embodiment, strains of cyanobacteria, algae, or other phototrophs lacking the PSII function take up externally supplied electrons. For example, in the MEPS system, a mutant of the cyanobacterium *Synechocystis* sp. PCC 6803 lacking PSII function is provided with electrons from an artificial water-oxidation catalyst, which are shuttled into the organism using chemical redox mediators.

TABLE 1

List of chemical mediators and potential natural electron acceptors, with the corresponding midpoint potentials ($E^0$,) and number of electrons transported (# $e^-$).

| Name | $E^0$, mV | # e- |
|---|---|---|
| Prospective Redox Mediators | | |
| Duroquinone | 5 | 2 |
| Plastoquinone variant | 80 | 2 |

TABLE 1-continued

List of chemical mediators and potential natural electron acceptors, with the corresponding midpoint potentials ($E^0$,) and number of electrons transported (# $e^-$).

| Name | $E^0$, mV | # e- |
|---|---|---|
| Benzoquinone | 280 | 2 |
| Methylene Blue | 11 | 2 |
| Thionine | 64 | 2 |
| Natural Electron Acceptors | | |
| Plastoquinone | 80 | 2 |
| Cytochrome $b_6f$ | >80 | 2 |

Figure 1:
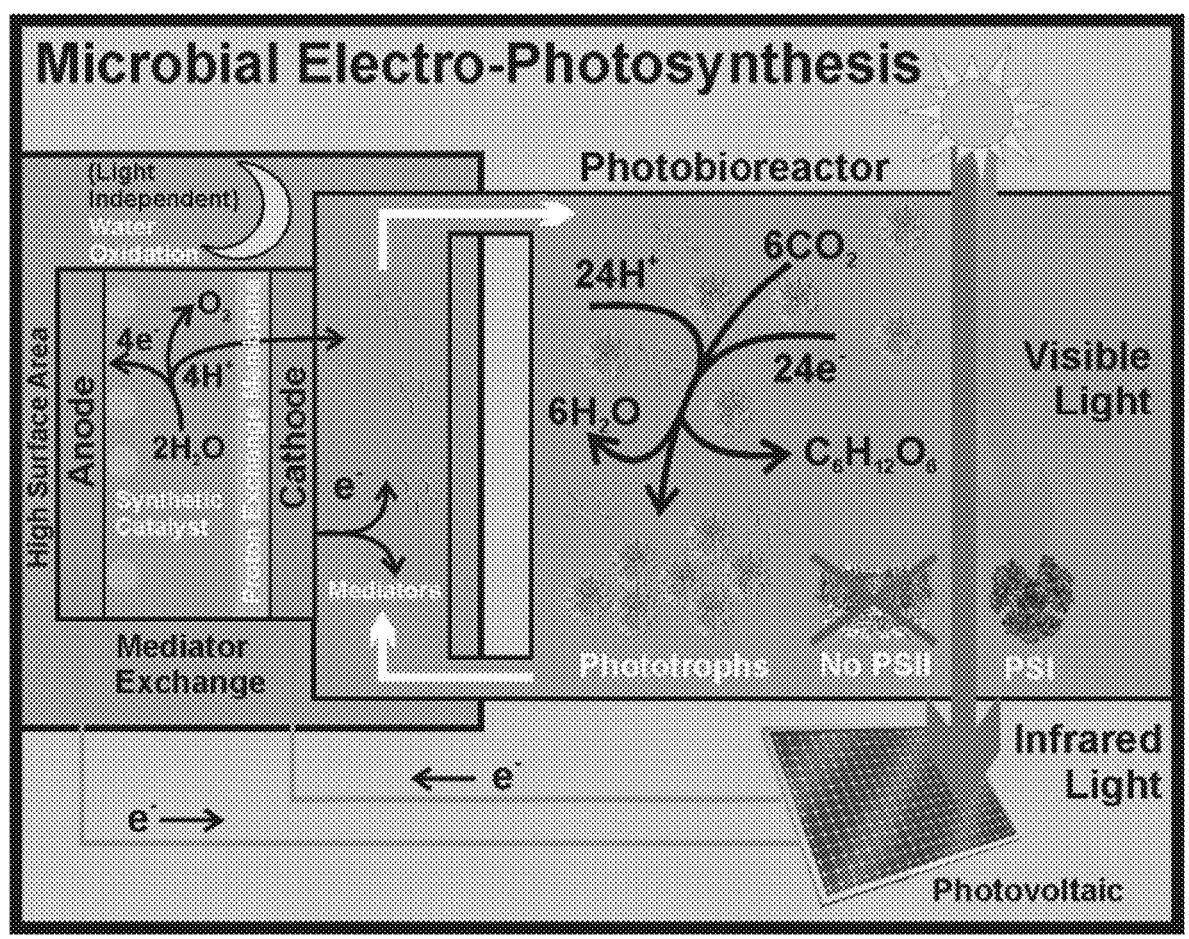
FIG. 1 depicts a schematic of microbial electro-photosynthesis (MEPS). PV-driven water oxidation generates electrons and protons to reduce chemical mediators. The mediators provide electrons to the photosynthetic electron transport chain to enable light-driven $CO_2$ fixation and growth of a photosynthetic microorganism lacking PSII function. In some embodiments, PV may be placed beneath the PBR to collect unused, transmitted light, which is predominantly composed of infrared light.

A system to perform MEPS is shown in FIG. 1. PV devices drive a synthetic catalyst to oxidize water (in place of PSII), and the extracted electrons and protons are used to reduce chemical redox mediators, such as those in Table 1 above. Oxidation of various mediators by the cyanobacteria is gauged by light-dependent current production and proportional activity of the photosynthetic electron transport chain.

The reduced mediators are pumped into a vertical tubular photobioreactor (PBR) for utilization by the cyanobacteria and oxidized mediators pumped out of the bottom of the PBR through a highly porous cathode for regenerating the mediators. A wide variety of existing PBR designs (e.g., horizontal tubular, airlift, flat panel, plastic-bag, etc.) could also be used.

Figure 4:
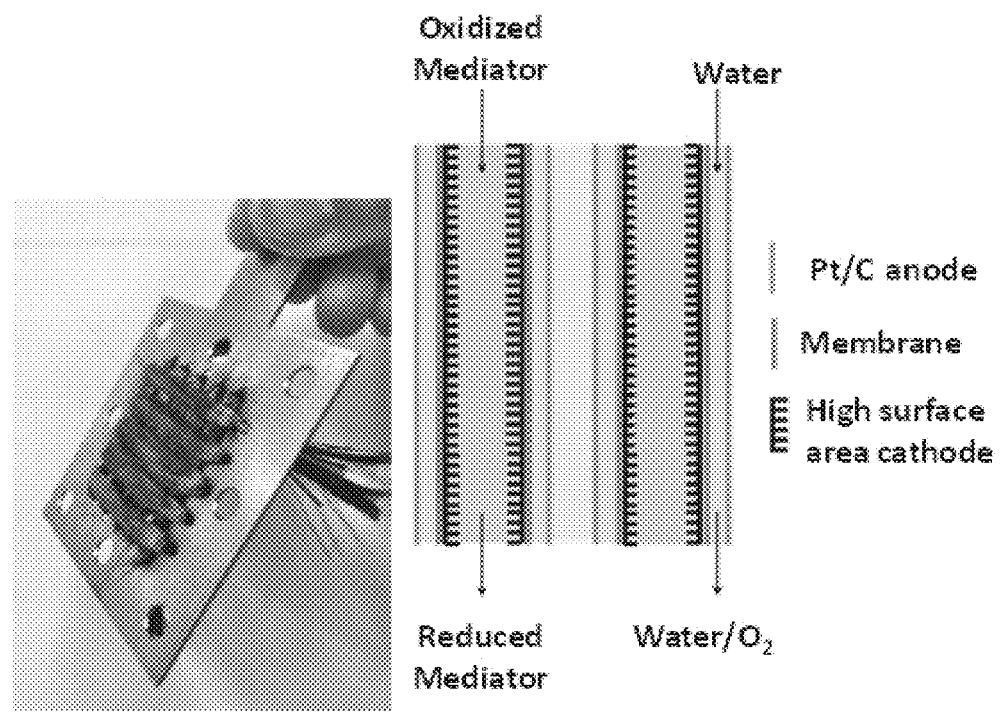
FIG. 4 depicts a high-surface-area cathode (left) and the electrochemical cell (right), where the high-surface-area cathode reduces the chemical mediator, the membrane allows passage of protons from the anode, and the platinum-carbon anode catalyzes water oxidation.

The cathode is made of high-surface-area carbon materials, such as carbon felt or carbon fibers, to maximize the volumetric current density of the electrochemical cell, as shown in FIG. 4. The cathode is <2 mm thick to minimize Ohmic losses. The electrode unit can be placed underneath the PBR unit or located in a centralized mediator regeneration facility. The anode consists of a platinum—carbon (Pt/C) electrode to oxidize water as a source of electrons, or any other water-oxidation catalyst, such as cobalt-phosphate and $C_{O3}O_4$ or $C_{O2}O_3$ nanoparticles. The anode and cathode are pressed into membrane/electrode assemblies that use proton exchange membranes (PEM) to separate the electrodes, as shown in FIG. 4.

Small quantities of oxygen are required to enable chlorophyll biosynthesis and respiration at night for sustained growth. In some embodiments, $O_2$ will be delivered at night or with the cathode potential turned off while $O_2$ is present to minimize mediator-catalyzed oxygen radical formation and current leading to $O_2$ reduction.

Non-Limiting Examples

We have engineered a strain of *Synechocystis* that lacks PSII function and is capable of photoheterotrophic growth, but not photoautotrophic growth and thus evolves no oxygen. Therefore, in the presence of light, but without organic carbon, these mutants accept electrons from the provided mediators to enable photoelectroautotrophic growth and $CO_2$ fixation. The growth rate of the mutant Synechocystis within MEPS is further improved using selective pressure for photoelectroautotrophic growth (i.e., growth due to both electric potential and light) by removing the supplied organic carbon (e.g., glucose), but retaining the presence of inorganic carbon (e.g., $CO_2$ or bicarbonate), reduced chemical mediators, and light. In some embodiments, the rate of improvement may be accelerated using mutagens, such as ultraviolet light and nitrosoguanidine. In other embodiments the cells will be maintained in the exponential growth phase by dilution with fresh media.

Figure 2:
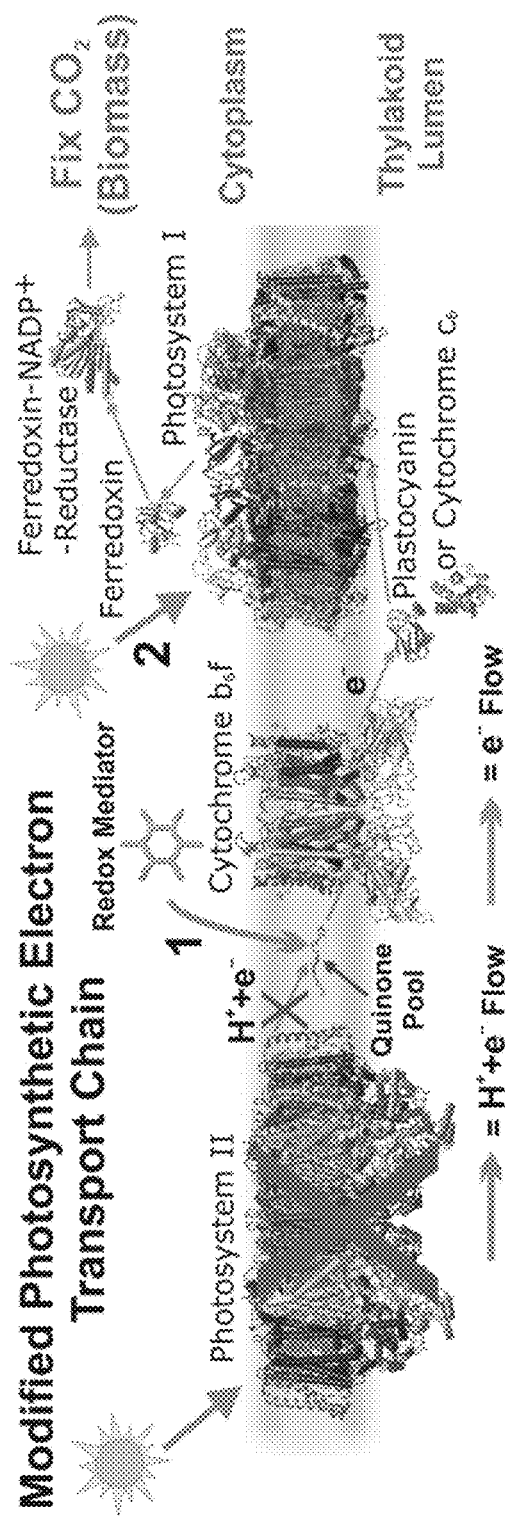
FIG. 2 illustrates a modified photosynthetic electron transport chain. The schematic shows how redox mediators provide electrons (and protons) to the photosynthetic electron transport chain (PETC) of the PSII-less photosynthetic microorganism. The mediator provides both electrons and protons to reduce plastoquinone to plastoquinol or directly transfer reducing equivalents to cytochrome $b_6f$. The electrons receive a boost in energy from PSI to enable $CO_2$ fixation, ATP production, and production of a desired product or biomass.

Strains with good photoelectroautotrophic growth characteristics are further modified to enhance their potential to produce products or fuel precursors, such as by means of free fatty acid production and excretion to reduce harvesting costs. MEPS systems may use platinum electrodes to oxidize water, or a number of other advanced catalysts available on the market or under development. MEPS replaces electrons provided by PSII with those provided externally as delivered by redox mediators. FIG. 2 shows how the mediators intercept the PETC of the mutant *Synechocystis*. While a number of redox mediator types may be used, quinone-type redox mediators with midpoint potentials near 0 mV may reduce plastoquinones or directly bind to cytochrome $b_6f$ to deliver its electrons and protons, thus, activating cytochrome $b_6f$ to pump protons for making ATP.

Advantages Over Current Technologies

MEPS provides the following improvements to existing technologies that use photosynthesis: 1) PV absorbs photons further into the infrared (700-1100 nm) than photosynthetic pigments (less than 700 nm), allowing for capturing about twice the number of photons compared to capture by photosynthetic microbes alone; the combined bio +PV system could have efficiencies >25%, or a >5X increase over bio alone. 2) Without PSII, PSI receives up to twice as many PAR photons, which would increase the fraction of photons converted to electrons for $CO_2$ fixation by another 30%, after accounting for additional cyclic electron transfer driven by PSI for producing ATP without the protons generated by PSII. Together 1 and 2 make significant improvements in utilizing the light energy for photosynthesis. 3) In place of PSII, MEPS establishes and regenerates a large pool of reduced chemical redox mediators that allow electrons to be taken up by the organism on demand. 4) Removing PSII from Synechocystis eliminates oxygen production, thus reducing the overall oxidative stress to the organism; also, PSII photoinhibition and repair no longer occur. 5) Oxygen-sensitive enzymes like hydrogenase, which are normally active only at low light levels, could be active throughout the day for producing fuel. 6) MEPS produces biomass and transportation fuel precursors, both of which are not efficiently generated from electricity alone.

Unlike traditional electrofuels, which make simple fuels from electricity, MEPS uses light energy to synthesize complex fuels and products with higher energy density that are compatible with existing infrastructure. Genetic engineering was used to remove PSII from *Synechocystis* and could allow for additional improvements to photosynthesis. Furthermore, new pathways could be introduced for increased biofuel production and excretion, converting our MEPS system into a microbial biofuel factory. The modular MEPS design allows for interchanging components (e.g., PBR, catalyst, source of electrons) and be driven by electricity from a variety of sources to leverage other developments in energy production. For example, transformation of *Synechocystis* sp. PCC 6803 with the thioesterase (fatB) gene from Umbellularia californica to produce laurate, and the native slr1609 gene coding for the acyl-ACP synthetase is deleted, which leads to a lack of laurate reincorporation and thereby excretion.

Current photosynthesis-based technologies rely on PSI and PSII for capturing PAR to drive carbon fixation. MEPS utilizes PV to oxidize water and to provide electrons to photosynthetic organisms in place of PSII; this represents a significant and innovative departure from conventional bioenergy technologies. With only PSI utilizing PAR photons, MEPS has the potential to increase the flux of the photosynthetic electron transport chain.

Electricity from PV does also need light, but can use IR (infrared) photons that are not useful for driving cyanobacterial photosynthesis. If the PV is placed below a thin PBR in a tandem design, it can absorb the IR photons passing through the PBR, which are not absorbed in natural photosynthesis (FIG. 1). These photons are about as numerous as PAR photons, and high-efficiency PV panels "shaded" by thin PBRs can provide about as many electrons as are needed for linear photosynthetic electron transport to NADP and $CO_2$ fixation.

Figure 5:
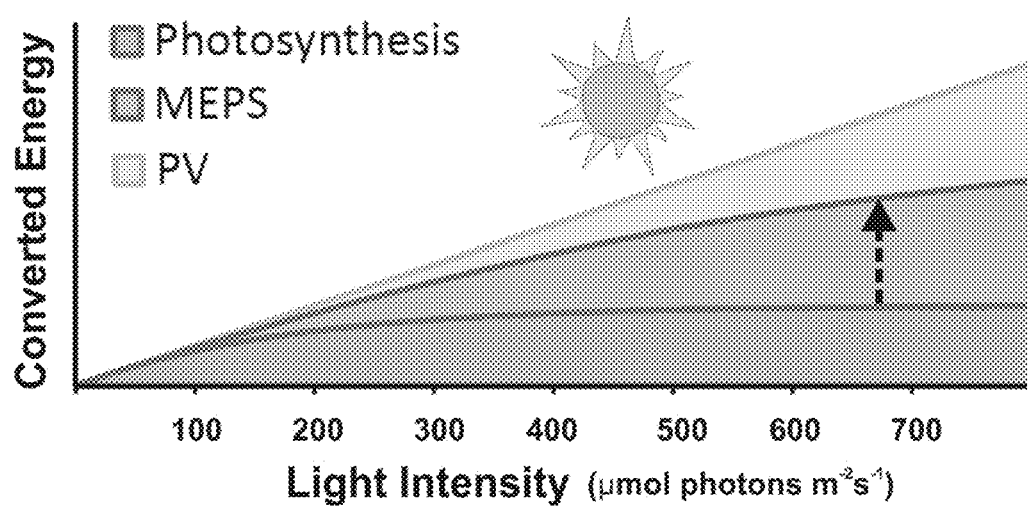
FIG. 5 illustrates light saturation in photosynthesis at modest light intensities. MEPS has the potential to capture and convert many more photons than natural photosynthesis under moderate to high light intensities.

Under full sunlight, about 90% of the PAR photons are wasted during natural photosynthesis. The loss of energy is a regulatory response primarily to protect the cell from reactive oxygen species (ROS) under light stress that can lead to cell death. By removing PSII and the corresponding light-dependent $O_2$ production, MEPS strains significantly reduce oxidative stress and eliminate the major need for the cell to dissipate this energy under high light. Without this constraint in MEPS, it may be possible to further streamline the photosynthetic regulatory process so that PSI can utilize significantly more photons for ATP synthesis and $CO_2$ fixation to catalyze additional growth at high light intensity, as shown in FIG. 5. Oxygen-sensitive enzymes like hydrogenase, which are normally active only at low light levels, could be active throughout the day and available to produce fuel. Furthermore, growing cultures under conditions associated with MEPS facilitates the selection of strains that best respond to using external electrons and are productive at low oxygen levels. Over time, natural selection exploits the advantages of photosynthesis at low oxygen levels in order to utilize electrons from artificial systems and correspondingly increase productivity.

Photosynthetic microorganisms have the capacity to produce significant quantities of transportation fuels while using marginal lands that do not compete with agricultural crops. Significantly increasing fuel productivity correspondingly reduces the water required per gallon of fuel. *Synechocystis* can also be grown using seawater to reduce freshwater needs.

Further enhancements may also be possible, by incorporating genes from other organisms to synthesize or overexpress other valuable bioproducts. Integrating the genetic changes of the *Synechocystis* evolved for growing on mediators into fatty acid excreting strains of *Synechocystis* allows for continuous production and harvesting of biofuels as a microbial factory. We currently have a strain of *Synechocystis* for excreting the high quality feedstock of laurate (C12), which is readily converted to synthetic paraffinic kerosene (SPK) by decarboxylation and isomerization using a catalyst at low cost. SPK is compatible with conventional gasoline engines and transportation infrastructure, and can be used in aircraft when blended with jet fuel (50% v/v). Together, these modifications demonstrate how critical it is to have a versatile genetic toolkit for optimizing biofuel and bioproduct production to ensure commercial viability.

The modularity of the MEPS design allows the various components (e.g., PBR, electrodes, catalyst, pumps, source of electrons and electricity) to be engineered and optimized independently, so they can be replaced with off-the-shelf components when possible. For example, the main PBR chamber could be replaced with many available designs, such as flat-panel, air-lift or plastic-bag PBRs. In this way, the rapid development of higher performance and lower cost components can be easily integrated to quickly improve overall economic viability. Similarly, the described MEPS design does not depend on the source of electrons provided to reduce the mediators. Anode respiring bacteria (ARB) are a class of bacteria that are able to deposit "spent" electrons on an anode from biodegradable organic compounds or biomass, often from wastewater. Mixed cultures of ARBs and non-ARBs, such as fermenters and methanogens, can work syntrophically to extract electrons from organic substrates and transfer them efficiently to the anode. These substrates could also come from photosynthetic organisms. Regardless of the source of electrons, they receive a boost in potential from a PV cell to reduce the mediators for MEPS.

A major advantage of the MEPS system is in its operational flexibility. Co-localizing PV with the MEPS helps to synchronize the energy inputs and keep photocurrent production in phase with biomass production. In addition, since photosynthesis only absorbs light up to 700 nm, PV could be installed beneath the PBRs to utilize the 700-1100 nm light to drive water oxidation (FIG. 1).

The current generated by the PV in a tandem cell design is adequate to drive MEPS without any additional land. Our modular MEPS design could also accept electricity from virtually any source. Utilizing grid power allows the PV to be installed at locations that may be less desirable for MEPS systems, such as residential or commercial rooftops and arid lands without access to water. In addition to PV, grid power can also be provided to MEPS by other renewable sources such as wind, geothermal, and hydroelectric power; MEPS allows for using this energy to directly make renewable fuels.

Operational costs for MEPS systems could also be reduced by co-locating with power plants, to utilize waste heat, water and $CO_2$ as well as electricity to drive the MEPS systems. Thus, MEPS could provide bioremediation capabilities by capturing and recycling waste $CO_2$ and provide an indirect route for converting hydrocarbons like natural gas and coal to high-value liquid transportation fuels.

The following claims are not intended to be limited by the examples and embodiments described above.

What is claimed is:

1. A microbial electrosynthesis cell apparatus comprising:
    a photobioreactor;
    a liquid disposed within the photobioreactor containing a microbe, wherein the microbe is an algae, comprising a mutation in a gene encoding a protein of Photosystem II (PSII), wherein PSII function in the microbe is minimal or absent;
    an electrode unit comprising an anode and a cathode, wherein the electrode unit is in fluid communication with the photobioreactor;
    a power source coupled to the electrode unit wherein, a source of electrons is generated in the electrode unit; and
    a redox mediator for shuttling electrons between the microbe and the cathode.

2. The apparatus of claim 1 wherein the photobioreactor is selected from the group consisting of a vertical tubular, air-lift, horizontal tubular, flat-panel, or plastic-bag photobioreactor.

3. The apparatus of claim 1 wherein the anode further comprises a catalyst to promote water oxidation to generate the electrons.

4. The apparatus of claim 3, wherein the catalyst is selected from the group consisting of platinum, platinum-carbon, cobalt phosphate, $C_{O3}O_4$ nanoparticles, and $C_{O2}O_3$ nanoparticles.

5. The apparatus of claim 1 wherein the cathode further comprises carbon felt or carbon fiber.

6. The apparatus of claim 1, wherein the power source is a photovoltaic device.

7. The apparatus of claim 1, wherein the source of electrons is provided by one or more of the group consisting of water oxidation, water electrolysis, hydrogen gas, hydrogen sulfide, the breakdown of organic waste, metal corrosion, cultures of anode respiring bacteria (ARB) and non-ARBs such as fermenters and methanogens that syntrophically breakdown organic waste.

8. The apparatus of claim 1, wherein the electrons are shuttled to the microbe using a redox mediator selected from the group consisting of duroquinone, trimethylquinone, 2,5 dimethylquinone, 2,6 dimethylquinone, 2,3 dimethylquinone, benzoquinone, 2,6-di-tert-butyl-1,4-benzoquinone, or ubiquinone.

9. The apparatus of claim 1, wherein the external electrons are shuttled to the microbe using a redox mediator selected from the group consisting of a plastoquinone (PQ) variant, where the native isoprenoid tail of PQ is replaced with an alkyl tail of 2, 3, 4, 5, 6, 7, 8 or 9 carbons.

10. The apparatus of claim 1, wherein the external electrons are shuttled to the microbe using a redox mediator selected from the group consisting of methylene blue, thionine, rezasurin or a protein redox mediator.

11. The apparatus of claim 6, wherein the photovoltaic device is located beneath the photobioreactor and configured to produce electricity using the light not absorbed by the microbe.

12. The apparatus of claim 1, wherein the electrode unit is configured to transfer reduced redox mediators into the photobioreactor and the photobioreactor is configured to transfer oxidized redox mediators back to the electrode unit.

13. The apparatus of claim 1, wherein the cathode is porous such that transfer of reduced redox mediators and oxidized redox mediators through the cathode occurs.

* * * * *